United States Patent
Kalgutkar et al.

(10) Patent No.: US 9,205,029 B2
(45) Date of Patent: Dec. 8, 2015

(54) DENTAL COMPOSITIONS WITH FLUORESCENT PIGMENT

(75) Inventors: Rajdeep S. Kalgutkar, Woodbury, MN (US); Gregory A. Kobussen, Woodbury, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 216 days.

(21) Appl. No.: 13/123,868

(22) PCT Filed: Oct. 9, 2009

(86) PCT No.: PCT/US2009/060082
§ 371 (c)(1),
(2), (4) Date: Apr. 12, 2011

(87) PCT Pub. No.: WO2010/045096
PCT Pub. Date: Apr. 22, 2010

(65) Prior Publication Data
US 2011/0200971 A1    Aug. 18, 2011

Related U.S. Application Data

(60) Provisional application No. 61/105,528, filed on Oct. 15, 2008.

(51) Int. Cl.
*A61K 6/083* (2006.01)
*A61K 6/00* (2006.01)

(52) U.S. Cl.
CPC .............. *A61K 6/0023* (2013.01); *A61K 6/0017* (2013.01); *A61K 6/0073* (2013.01); *A61K 6/083* (2013.01); *A61K 6/0094* (2013.01)

(58) Field of Classification Search
CPC ............................ A61K 6/0094; A61K 6/083
USPC ........................................................ 523/115
See application file for complete search history.

(56) References Cited

U.S. PATENT DOCUMENTS

| | | |
|---|---|---|
| 2,938,873 A | 5/1960 | Kazenas |
| 3,412,035 A | 11/1968 | Mcintosh |
| 3,412,036 A | 11/1968 | Mcintosh |
| 3,741,907 A | 6/1973 | Beyerlin |
| 3,915,884 A | 10/1975 | Kazenas |

(Continued)

FOREIGN PATENT DOCUMENTS

| | | |
|---|---|---|
| DE | 10146883 | 4/2003 |
| EP | 0173567 | 3/1986 |

(Continued)

OTHER PUBLICATIONS

Berlman, Isadore B., "Handbook of fluorescence spectra of aromatic molecules", $2^{nd}$ Edition, (1971).

(Continued)

*Primary Examiner* — Michael Pepitone
(74) *Attorney, Agent, or Firm* — 3M Innovatie Properties Company; Eric E. Silverman (57) ABSTRACT

The invention features a dental composition containing a fluorescent organic pigment, e.g. a hydroxyl substituted aryl guanamine an or a fluorescent compound encapsulated in a thermo plastic or thermo set polymer, in an amount that provides the composition with fluorescence resembling that of natural teeth.

24 Claims, 1 Drawing Sheet

(56) References Cited

U.S. PATENT DOCUMENTS

| | | | |
|---|---|---|---|
| 3,922,232 A * | 11/1975 | Schein | 252/301.35 |
| 4,259,075 A | 3/1981 | Yamauchi | |
| 4,298,738 A | 11/1981 | Lechtken et al. | |
| 4,324,744 A | 4/1982 | Lechtken et al. | |
| 4,356,296 A | 10/1982 | Griffith et al. | |
| 4,385,109 A | 5/1983 | Lechtken et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,642,126 A | 2/1987 | Zador et al. | |
| 4,648,843 A | 3/1987 | Mitra | |
| 4,652,274 A | 3/1987 | Boettcher et al. | |
| 4,695,251 A | 9/1987 | Randklev | |
| 4,710,523 A | 12/1987 | Lechtken et al. | |
| 4,737,593 A | 4/1988 | Ellrich et al. | |
| 4,872,936 A | 10/1989 | Engelbrecht | |
| 5,076,844 A | 12/1991 | Fock et al. | |
| 5,102,461 A * | 4/1992 | Rheinberger et al. | 106/35 |
| 5,130,347 A | 7/1992 | Mitra | |
| 5,154,762 A | 10/1992 | Mitra et al. | |
| 5,501,727 A | 3/1996 | Wang | |
| 5,530,038 A | 6/1996 | Yamamoto et al. | |
| 5,545,676 A | 8/1996 | Palazzotto et al. | |
| 6,030,606 A | 2/2000 | Holmes | |
| 6,251,963 B1 | 6/2001 | Kohler et al. | |
| 6,306,926 B1 | 10/2001 | Bretscher et al. | |
| 6,387,981 B1 | 5/2002 | Zhang et al. | |
| 6,458,868 B1 | 10/2002 | Okada et al. | |
| 6,572,693 B1 | 6/2003 | Wu et al. | |
| 6,730,156 B1 | 5/2004 | Windisch et al. | |
| 6,765,036 B2 | 7/2004 | Dede et al. | |
| 6,899,948 B2 | 5/2005 | Zhang et al. | |
| 7,114,951 B2 | 10/2006 | Sun et al. | |
| 7,137,818 B2 | 11/2006 | Savic et al. | |
| 2003/0036582 A1 | 2/2003 | Yamakawa | |
| 2003/0166740 A1 | 9/2003 | Mitra | |
| 2003/0195273 A1 | 10/2003 | Mitra | |
| 2004/0137409 A1* | 7/2004 | Savic et al. | 433/203.1 |
| 2005/0252413 A1 | 11/2005 | Kangas et al. | |
| 2005/0252414 A1 | 11/2005 | Craig | |
| 2005/0256223 A1 | 11/2005 | Kolb et al. | |
| 2005/0272334 A1* | 12/2005 | Wang et al. | 442/93 |
| 2006/0194895 A1* | 8/2006 | Loveridge et al. | 523/115 |
| 2006/0241205 A1* | 10/2006 | Jia | 523/115 |
| 2007/0232718 A1 | 10/2007 | Jia et al. | |
| 2010/0063176 A1 | 3/2010 | Kato | |
| 2010/0184882 A1 | 7/2010 | Yasuhiro | |
| 2011/0172323 A1 | 7/2011 | Akizumi | |

FOREIGN PATENT DOCUMENTS

| | | |
|---|---|---|
| EP | 0189540 | 8/1986 |
| EP | 0201031 | 11/1986 |
| EP | 0201778 | 11/1986 |
| EP | 0238025 | 9/1987 |
| EP | 0373384 | 6/1990 |
| EP | 0712622 | 5/1996 |
| EP | 1051961 | 11/2000 |
| GB | 1112987 | 5/1968 |
| GB | 1428672 | 3/1976 |
| JP | S49-030468 | 3/1974 |
| JP | 2002-255722 | 9/2002 |
| JP | 2010-037254 | 2/2010 |
| SU | 212171 | 1/1968 |
| WO | 00-38619 | 7/2000 |
| WO | 00-42092 | 7/2000 |
| WO | 01-07444 | 2/2001 |
| WO | 01-92271 | 12/2001 |
| WO | 03-063804 | 8/2003 |
| WO | 2006-122081 | 11/2006 |
| WO | 2007-041477 | 4/2007 |
| WO | 2008-083067 | 7/2008 |

OTHER PUBLICATIONS

Yen, William et al., "Inorganic Phosphors—Compositions, Preparation and Optical Properties", The CRC Press, Laser and Optical Science and Technology Series, (2004).
Gutcho, M.H., "Microcapsules and Microencapsulation Techniques", (1976).
Mathiowitz, E., Encyclopedia of Controlled Delivery, "Microencapsulation to Mucosal Drug Delivery, Vaginal Drug Delivery, and Treatment Modalities", vols. 1-2, p. 493-504 (1999).
CIE Technical Report, "Colorimetry", CIE 15:2004, $3^{rd}$ edition.
Adamson. Journal of the Chemical Society, Part V, (1949) p. S144-S155.
Odian, G., "Principles of Polymerization", $4^{th}$ ed. (2004).
Wyszecki, G., et al., "Color Science—Concepts and Methods, Quantitative Data and Formulae" $2^{nd}$ edition, Section 3.3.8, (1982).
Hunter, R.S., "The Measurement of Appearance", $2^{nd}$ Edition, p. 322 (1987).
Mekler, V.M., "A Photochemical Technique to Enhance Sensitivity of Detection of Fluorescence Resonance Energy Transfer", Photochemistry and Photobiology, vol. 59, No. 6, p. 615-620 (1994).
PCT International Search Report for PCT Application No. PCT/US2009/060082 mailed Jun. 2, 2010.
PCT Written Opinion of the International Searching Authority for PCT Application No. PCT/US2009/060082 mailed Jun. 2, 2010.
U.S. Appl. No. 60/437,106; Abuelyaman, Ahmed, filed Dec. 30, 2002.
U.S. Appl. No. 60/600,658; Luchterhandy, Thomas; filed Aug. 11, 2004.
U.S. Appl. No. 60/984,785; Kalgutkar, Rajdeep; filed Nov. 2, 2007.
Database Caplus US; 2003, Xu, Li-he: "Fluorescent pigment 6-phenyl1,3,5-triazine-2,4-diamine were synthesized from benzonitrile and cyanoguanidine, and its heat resistance was studied." Database accession No. 2005:514254.

* cited by examiner

Fig. 1

DENTAL COMPOSITIONS WITH FLUORESCENT PIGMENT

CROSS REFERENCE TO RELATED APPLICATIONS

This application is a national stage filing under 35 U.S.C. 371 of PCT/US2009/060082, filed Oct. 9, 2009, which claims priority to U.S. Application No. 61/105,528, filed Oct. 15, 2008, the disclosure of which is incorporated by reference in its/their entirety herein.

TECHNICAL FIELD

The invention generally relates to dental compositions that contain an organic fluorescent pigment.

BACKGROUND

Over the past several decades, there has been an increasing demand among dentists and dental patients for more aesthetic dental restorations. High aesthetic quality is particularly important for easily visible restorations, such as those involving the front teeth, but may also be desirable for restorations involving teeth that are not as readily visible.

The dental industry's growing focus on aesthetic dentistry has led to the development of dental restorative compositions that more closely mimic the appearance of natural teeth. For example, tooth-colored, composite resin materials have been developed that can be used in place of, for example, metal amalgam fillings, to provide more natural looking dental restorations. In recent years, highly aesthetic composite materials, such as 3M ESPE™ FILTEK™ Supreme Plus Universal Restorative (3M Company, St. Paul, Minn.), have become available with shading systems and opacity options that make it possible for a dentist to create dental restorations so natural looking they are virtually undetectable to the casual observer.

Since human teeth fluoresce when irradiated with ultraviolet (UV) light, dental restorations that fail to exhibit fluorescence similar to that of natural teeth may become more noticeable when viewed under UV radiation or "black light" conditions. For example, dental restorative compositions that use resin systems that do not fluoresce as intensely as natural teeth and/or that contain components, such as color stabilizers, that diminish the fluorescence of the composition, may provide restorations that appear darker than surrounding teeth under UV light. Conversely, dental compositions that contain components with greater fluorescence than that of natural teeth may appear brighter than surrounding teeth under these conditions. Consequently, restorations made with such compositions, even if undetectable under normal visible light or full spectrum lighting conditions, may suffer from reduced aesthetic quality when exposed to UV light. As restorative dentistry has become increasingly focused on aesthetics of restorations, there is an increasing demand for aesthetic fluorescent composites that match natural tooth fluorescence.

SUMMARY

The invention features hardenable dental compositions and methods that provide dental restorations having natural tooth fluorescence. This allows for the creation of aesthetic dental restorations that keep their natural-looking appearance even when viewed under UV radiation or black light.

The compositions of the invention typically comprise a resin system that includes a polymerizable component combined with an initiator system. The polymerizable component typically comprises at least one ethylenically unsaturated compound, such as a (meth)acrylate, and the initiator system typically comprises one or more electron donors. The compositions also contain an organic fluorescent pigment component that serves as a fluorescing agent that, when present in an appropriate amount, provides the composition with fluorescence mimicking that of natural teeth. The exact amount of fluorescing agent in the compositions will vary depending upon the particular organic fluorescent pigment(s) used and the nature of the other components present in the composition, but generally ranges from about 10 ppm to about 10,000 ppm when measured using the test methods described herein.

Suitable organic fluorescent pigment components may be in the form of, for example, insoluble finely divided powders, fluorescent compounds attached to a polymer backbone, and/or fluorescent compounds encapsulated in thermoset or thermoplastic materials and combinations thereof.

The dental compositions of the invention may also optionally include a filler system. In some implementations, the filler system includes one or more silane-treated nanofillers, selected from nano silica, nano zirconia, zirconia-silica nanoclusters, and combinations thereof.

In another aspect, the invention provides a method of making of dental composition having natural tooth fluorescence, which method involves the steps of: (a) providing a dental resin system that, when cured, has non-natural tooth fluorescence, (b) adding a sufficient amount of an organic fluorescent pigment to the resin system to provide a composition having a natural tooth fluorescence, and (c) optionally comparing the fluorescence of the composition to the fluorescence of a natural tooth.

The dental compositions of the invention are useful in a variety of dental and orthodontic applications, including as dental restoratives, dental adhesives, dental cements, cavity liners, orthodontic adhesives, dental sealants, dental coatings, and the like. The compositions and related methods may be used to prepare dental articles by hardening to form, for example, dental fillings, dental mill blanks, dental crowns, dental prostheses, orthodontic devices, and the like.

An advantage of some embodiments of the invention is greater stability against loss of fluorescence on exposure to sustained ultraviolet light than that exhibited by dental composites containing organic fluorescent dyes. The compositions of the invention, in some implementations, are also substantially more aesthetic than dental composites containing inorganic pigments. In addition, a relatively small amount (e.g., 50 to 2000 ppm) may be sufficient in some cases to provide the composition with suitable fluorescence.

The above summary is not intended to describe each embodiment or every implementation of the invention. Other embodiments, features, and advantages of the present invention will be apparent from the following detailed description thereof, and from the claims.

DEFINITIONS

As used herein, the phrase "natural tooth fluorescence" means that when viewed under ultraviolet light of 365 nm the composition exhibits a fluorescence intensity and color resembling that of a natural tooth. Although the fluorescence of natural teeth varies from subject to subject and the desired closeness of the match of the composition's fluorescence to that of a natural tooth depends on the precise situation and/or aesthetic demands of the patient (e.g., molars and other teeth that are not easily visible may not need to match the natural tooth fluorescence as closely as front teeth). Typically, the compositions of the invention exhibit a fluorescence intensity in the range of about 20 counts per second to about 100 counts per second, more typically from about 30 counts per second to about 90 counts per second, and most typically from about 35 counts per second to about 85 counts per second.

By "non-natural tooth fluorescence" is meant fluorescence that is visibly less intense or more intense than the fluorescence exhibited by natural teeth, or exhibits a significantly different florescence color than that of natural teeth. When used in reference to an electron donor component (e.g. "an electron donor with non-natural tooth fluorescence," etc.), the term means that when the electron donor is compounded with the other components of the composition and the composition is subsequently cured, its fluorescence is visibly different in intensity or wavelength than that of natural teeth. By "non-fluorescent" is meant that when irradiated with UV radiation, the compound, composition, or material exhibits no visible fluorescence or is only weakly fluorescent, i.e. substantially below the fluorescence exhibited by a natural human tooth such that the difference is easily visible.

By "organic fluorescent pigment" is meant a material that (1) is an organic molecule (e.g. polymer) that either encapsulates or is attached to a fluorescent dye or compound or is itself an intrinsically fluorescent molecule and (2) is substantially insoluble in the dental resin system. A dye, by comparison, is substantially soluble in the dental resin.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking.

By "dental composition" is meant an unfilled or filled (e.g. a composite) material (e.g., a dental or orthodontic material) that are capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure.

By "hardenable dental composition" is meant a dental composition, such as a paste, that can be hardened to form a dental article.

By "dental article" is meant an article that can be adhered (e.g., bonded) to an oral surface (e.g., a tooth structure). Typically, the dental article is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, the terms "dental composition" and "dental article" are not limited to compositions and articles used in dental applications, but also include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like), respectively.

By "oral surface" is meant a soft or hard surface in the oral environment. Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters. By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" is synonymous with "nanosized particles," and refers to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are comprises of discrete, non-aggregated and non-agglomerated particles.

By "nanocluster" is meant an association of nanoparticles drawn together by relatively weak intermolecular forces that cause them to clump together, i.e. to aggregate. Typically, nanoclusters have an average size of at most 10 micrometers.

As used herein, the term "ethylenically unsaturated compound" is meant to include monomers, oligomers, and polymers having at least one ethylenic unsaturation.

By "polymerization" is meant the forming of a higher weight material from monomer or oligomers. The polymerization reaction also can involve a cross-linking reaction.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

The terms "comprises", "comprising" and variations thereof do not have a limiting meaning where these terms appear in the description and claims.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The invention features polymerizable fluorescent dental compositions that contain an organic fluorescent pigment. It has been found, surprisingly, that the incorporation of fluorescent organic pigments into a dental composition can give greater durability of fluorescence than many fluorescent dyes, even though such pigments typically comprise encapsulated fluorescent dyes in a crosslinked polymer matrix. In addition, certain organic pigments can be added to a dental composite without causing a significant change in the optical characteristic of the material, such as CIELAB (i.e. CIE 1976 L*a*b* color space: a uniform-color space utilizing an Adams-Nickerson cube root formula, suggested in 1974 for adoption by the Commission Internationale de l'Eclairage or the International Commission on Illumination (CIE) in 1976 for use in the measurement of small color differences" (*The Measurement of Appearance*, pg322, R. S. Hunter)) parameters or contrast ratio, and particle size of the pigment does not appear to be a substantial factor in the aesthetics. Pigments with a median particle size of 10 microns do not seem to increase light scattering. As a result, the incorporation of fluorescent organic pigments at very low levels results in acceptably stable and aesthetic fluorescent composites with mechanical properties comparable to controls with no fluorescence. A concentration of fluorescent organic pigment as little as 50 to 20000 ppm range is effective to provide an A3 shaded dental restorative. This is far lower than the concentration needed for inorganic pigments.

The organic fluorescent pigment used in the dental compositions of the invention may be combined with one or more additional fluorescent agents, which may be selected from the group including, but not limited to, other organic fluorescent pigments, inorganic fluorescent pigments, and organic fluorescent dyes. Numerous examples of suitable classes of organic fluorescent dyes may be found in "Handbook of fluorescence spectra of aromatic molecules" by Isadore B. Berlman, 2nd ed., Academic Press, 1971 as well as in U.S. Pat. Nos. 7,137,818 and 7,114,951. Numerous examples of suitable inorganic luminescent pigments may be found in "Inorganic Phosphors" by William Yen and Marvin Weber, CRC Press, 2004. The additional luminescent agent may, if desired, be selected so as not to negatively affect any aesthetic and functional property described herein.

The incorporation of an organic fluorescent pigment as a fluorescing agent at a suitable concentration provides dental compositions and materials with fluorescence mimicking that of natural teeth. Natural tooth fluorescence is particularly desirable for resin/filler composite materials used in restorative dentistry where the aesthetic quality of the material is often important. Such compositions typically include a polymerizable component, an initiator system, one or more fillers and/or other additives depending on the desired application. Organic fluorescent pigments are advantageous as fluorescing agents in these compositions because they can be used in relatively low concentrations, and generally do not affect the opacity of dental composites.

Polymerizable Component

The dental compositions of the present invention are hardenable, typically due the presence of a polymerizable component. In some embodiments, the compositions can be hardened (e.g., polymerized by conventional photopolymerization and/or chemical polymerization techniques) prior to applying it to an oral surface. In other embodiments, the compositions can be hardened (e.g., polymerized by conventional photopolymerization and/or chemical polymerization techniques) after it has been applied to an oral surface.

In certain embodiments, the compositions are photopolymerizable, i.e., the compositions contain a photoinitiator system that upon irradiation with actinic radiation initiates the polymerization (or hardening) of the composition. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The compositions, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and/or NPGDMA (neopentylglycol dimethacrylate). Various combinations of these hardenable components can be used if desired.

When the composition contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present invention typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth) acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658 (Luchterhandt et al.), filed on Aug. 11, 2004. The compositions may also include a mixture of ethylenically unsaturated compounds both with and without acid functionality.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present invention typically include at most 80% by weight, more typically at most 70% by weight, and most typically at most 60% by weight ethylenically unsaturated compounds with acid functionality, based on the total weight of the unfilled composition.

Initiator System

In certain embodiments, the compositions of the present invention are photopolymerizable, i.e., the compositions contain a photopolymerizable component and a photoinitiator system that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions.

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the composition.

The reducing or oxidizing agents can be microencapsulated as described in U.S. Pat. No. 5,154,762 (Mitra et al.). This will generally enhance shelf stability of the composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, including photoinitiator systems or with a composition such as described U.S. Pat. No. 5,154,762 (Mitra et al.).

Fluorescent Organic Pigment Component

The compositions of the invention include at least one fluorescent organic pigment component, which serves as a fluorescing agent to provide the composition, and/or a hardened product or material (e.g. a dental restoration) made from the composition, with natural tooth fluorescence.

Organic fluorescent pigments suitable for use in the invention may be divided into at least three major types. In all cases the fluorescent pigment is distinguished from a dye by being substantially insoluble in the resin system, which typically comprises a free radically polymerizable monomer. The first class of fluorescent pigments is fluorescent compounds that are used in the form of insoluble finely divided powders. Examples of classes of such compounds include, but are not limited to, coumarins, naphthalimides, xanthenes, thioxanthenes, naphtholactams, oxazines, thiazines, oxazoles, benzoxazoles, furans, benzofurans, pyrazolines, stilbenes, distyrylbenzenes, distyrylbiphenyls, benzimidazoles, 1,3,5-triazin-2yl derivatives, aryl benzoguanamines and polycyclic aromatic hydrocarbons. It is known to those skilled in the art that each of the above classes can be derivatized with functional groups such as amides, sulfonates or carboxy groups such that the compound is rendered substantially insoluble in typical free radically polymerizable monomers. The second class of fluorescent pigments includes derivatives of the above classes of fluorescent compounds covalently bonded to a polymer backbone. Additional classes of fluorescent compounds are disclosed in "Handbook of fluorescence spectra of aromatic molecules" by Isadore B. Berlman, 2nd ed., Academic Press, 1971 as well as in U.S. Pat. Nos. 7,137,818 and 7,114,951. Polymer backbones to which the aforesaid classes of fluorescent compounds may be attached are known to those skilled in the art and may include but are not limited to polyacrylates, polyethers, polyurethanes, polyamides and polyesters. Additional examples of condensation and addition polymer backbones may be found in Principles of Polymerization, $4^{th}$. ed by George B. Odian, John Wiley & Sons (2004). The third class of fluorescent pigments includes, but is not limited to, the above classes of fluorescent compounds encapsulated in thermoset or thermoplastic polymer matrices. Examples of such polymer matrices include, toluene-sulfonamide-melamine-formaldehyde resin matrix, polyamides, polyurethanes, polyesters although other polymer matrices can be anticipated by those skilled in the art. The method of preparing such encapsulated fluorescent pigments may involve polymerization of the matrix in the presence of the fluorescent compound followed by milling to a finely divided powder (U.S. Pat. Nos. 2,938,873, 3,412,036, 3,915,884, 3,922,232, 3,741,907) or by means of suspension polymerization to yield spherical encapsulated fluorescent pigments (U.S. Pat. No. 3,412,035). It is known to those skilled in the art that when polymeric backbones or encapsulants are present that these materials typically will not absorb incident ultraviolet light such that the fluorescence efficiency of the pigments will be significantly diminished.

Also the fluorescent pigments available from DayGlo Corp. (Cleveland, Ohio), J. Color Chemicals Corp (Hangzhou, China), Organic Dyestuffs Corp. (East Providence, R.I.), Beaver Luminescers (Newton, Mass.) are suitable provided that the selected pigment must be able to provide a hardened dental composition that exhibits natural tooth fluorescence. Useful fluorescent pigments also include those commercially known as "invisible fluorescent pigments".

The fluorescent organic pigments are typically present at about 10 ppm to about 10,000 ppm weight percent, more typically about 20 ppm to about 5000 ppm weight percent, and most typically about 50 ppm to about 2000 ppm weight percent, based on the overall composition. An advantage of some embodiments of the invention is that it allows one to add stable fluorescence to formulations regardless of the rest of the formulation, such as the UV stabilizer (e.g. tinuvin 796) concentration.

Filler(s)

The compositions of the present invention may optionally contain one or more fillers. Fillers may be selected from one or more of a wide variety of materials suitable for incorporation in compositions used for dental applications, such as fillers currently used in dental restorative compositions, and the like.

The choice of the filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler that is incorporated into the composite, referred to herein as the "loading level" and expressed as a weight percent based on the total weight of the dental material, will vary depending on the type of filler, the curable resin and other components of the composition, and the end use of the composite.

For some dental materials, such as sealants, the compositions of the invention can be lightly filled (e.g., having a loading level of less than about 40 weight percent) or unfilled. In such implementations, the viscosity of the dental material is sufficiently low to allow its penetration into pits and fissures of occlusal tooth surfaces as well as into etched areas of enamel, thereby aiding in the retention of the dental material.

In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level is generally at least 40 weight percent, and more typically is between about 60 and 90 weight percent.

The filler(s) used in the compositions of the invention is typically finely divided. The filler(s) can have a unimodial or polymodial (e.g., bimodal) particle size distribution. The maximum particle size (the largest dimension of a particle, generally, the diameter) of the filler(s) is typically less than 20 micrometers, more typically less than 10 micrometers, and most typically less than 5 micrometers. The average particle size of the filler(s) is typically less than 0.1 micrometers, and more typically less than 0.075 micrometer.

The filler(s) may be an inorganic material. It may also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

Examples of suitable inorganic fillers are naturally occurring or synthetic materials including, but not limited to: quartz (i.e. silica, $SiO_2$); nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). In some embodiments, the silica or nanosilica particles are non-pyrogenic, i.e. comprise non-fumed silica. Examples of suitable organic filler particles include filled or unfilled pulverized olycarbonates, polyepoxides, and the like.

The filler may be acid-reactive, non-acid-reactive, or a combination thereof. Suitable non-acid-reactive filler particles include quartz, submicron silica, nano silica, nano zirconia, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments. In some implementations of the invention, the filler system may contain a combination of at least one filler comprising heavy metal oxide nanoparticles (e.g., zirconia nanoparticles), and/or at least one filler comprising non-heavy metal oxide particles (e.g. silica nanoparticles), and/or at least filler comprising a heavy metal oxide and a non-heavy metal oxide (e.g. clusters of zirconia and silica nanoparticles).

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

In some implementations, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass, if present, typically contains sufficient elutable cations so that a hardened dental composition will form when the glass is mixed with the components of the hardenable composition. The glass also typically contains sufficient elutable fluoride ions so that the hardened composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other cement components and will perform well when the resulting mixture is used in the mouth.

Generally, the average particle size (typically, diameter) for FAS glass used in such compositions is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEM-FIL Superior (Dentsply International, York, Pa.). Mixtures of fillers can be used if desired.

The surface of the filler particles can also be treated with a coupling agent in order to enhance the bond between the filler and the resin. Suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$-$SiO_2$) fillers and nanofillers, silane-treated silica fillers and nanofillers, silane-treated zirconia fillers and nanofillers, and combinations thereof are especially suitable for certain restorative compositions.

Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof.

In some implementations of the invention, the compositions are non-aqueous. In other implementation, the compositions may optionally contain water. The water can be distilled, deionized, or plain tap water. If present, the amount of water should be sufficient to provide adequate handling and mixing properties and/or to permit the transport of ions, particularly in a filler-acid reaction. In such embodiments, water represents at least about 1 wt-%, and more preferably at least about 5 wt-%, of the total weight of ingredients used to form the hardenable composition. Generally, water represents no greater than about 75 wt-%, and more preferably no greater than about 50 wt-%, of the total weight of ingredients used to form the hardenable composition.

If desired, the compositions of the invention may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The dental compositions of the present invention can be prepared by combining all the various components using conventional mixing techniques. The resulting composition may optionally contain fillers, solvents, water, and other additives as described herein. Typically, photopolymerizable compositions of the invention are prepared by simply admixing, under "safe light" conditions, the components of the inventive compositions. Suitable inert solvents may be employed if desired when affecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the iodonium complex salt, sensitizer, and electron donor in the polymerizable resin, with or without the use of mild heating to facilitate dissolution.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation. Also, for those implementation in which the dental composition is a resin-modified glass ionomer (RMGI), the polyacid, acid-reactive filler and water generally would not all be present in the same part, although any two of these may be grouped together in the same part along with any combination of other components.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions. The compositions may be in the form of composites or restoratives that adhere very well to dentin and/or enamel. Optionally, a primer layer can be used on the tooth tissue on which the hardenable composition is used.

The invention encompasses a wide variety of dental compositions, which may be filled or unfilled. Exemplary dental materials include dental restoratives (e.g., composites, fillings, sealants, inlays, onlays, crowns, and bridges), orthodontic appliances, and orthodontic adhesives. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth.

The features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

As used herein,

"CAMP" refers to 1-(2-methacryloyloxyethyl)-2-(7-methylene-1,5, dithiaoctan-3-yl) phalate, prepared as described in Example 1 of WO/US2006/122081;

"TrisMAP" refers to 244-(2-hydroxy-3-methacryloxypropoxy)phenyl-2-[4-(2-[2-methacryloxyethoxy]phthalyloxy-3-methacryloxypropoxy)phenyl]-propane. Prepared essentially as described in U.S. Provisional Application No. 60/984,785 filed Nov. 2, 2007 (Kalgutkar et al.)

"UDMA" refers to diurethane dimethacrylate, obtained under the trade designation "ROHAMERE 6661-0" from Rohm America LLC, Piscataway, N.J.;

"BisEMA6" refers to ethoxylated bisphenol A dimethacrylate, obtained from Sartomer Co., Inc., Exton, Pa.;

"TEGDMA" refers to triethyleneglycol dimethacrylate, obtained from Sartomer Co., Inc., Exton, Pa.;

"BisGMA" refers to 2,2-bis[4-(2-hydroxy-3-methacryloyloxypropoxy)phenyl]propane;

"BHT" refers to butylated hydroxytoluene;

"SiO2/ZrO2 Filler 1" refers to silane-treated zirconia-silica nanocluster filler prepared essentially as described in U.S. Pat. No. 6,730,156 and surface treated as described below;

"SiO2/ZrO2 Filler 2" refers to silane-treated zirconia-silica nanocluster filler prepared essentially as described in U.S. Pat. No. 6,730,156 and surface treated as described below;

"SiO2/ZrO2 Filler 3" refers to silane-treated zirconia-silica nanocluster filler prepared essentially as described in U.S. Pat. No. 6,730,156

"ZrO2 Filler" refers to a silane-treated nano-sized zirconia prepared essentially as described in Preparatory Example 1A in U.S. Patent Publication No. 2005/0252413, except that GF31 was used instead of a blend of A-174 and A-1230;

"SiO2 Filler" refers to a silane-treated nano-sized silica having a nominal particle size of approximately 20 nanometers, prepared essentially as described for FILLER F in U.S. Patent Publication No. 2005/0252413?

"ENMAP" refers to Ethyl-(N-methyl-N-phenyl)amino propionate prepared by Michael addition of N-methylaniline to ethyl acrylate (J. Chem. Soc., Supplement, p. 144-152 (1949)), 63524US002;

"EDMAB" refers to ethyl 4-dimethylaminobenzoate;

"EDMOA" refers to 2-ethyl-9,10-dimethoxyanthracene;

"DPIPF6" refers to diphenyliodonium hexafluorophosphate, obtained from Alfa Aesar, Ward Hill, Mass.;

"CPQ" refers to camphorquinone;

"Irgacure 819" refers to a Bis(2,4,6-Trimethylbenzoyl) phenylphosphine oxide obtained from Ciba, Inc., Tarrytown, N.Y.;

"TINUVIN" refers to a polymerizable UV stabilizer obtained under the trade designation TINUVIN R 796 from Ciba Specialty Chemicals, Tarrytown, N.Y.;

"L-88" refers to an organic fluorescent pigment obtained from Beaver Luminescers (Newton, Mass.);

"QBK58/UF-A2" refers to $Y_2SiO_5$:Ce obtained from Phosphor Technology (Stevenage, Hertfordshire, England);

"A-594-5" or "A-594" refers to a fluorescent pigment obtained from DayGlo Corp, Cleveland, Ohio;

"Lumilux White" refers to Lumilux Natural White Z which was obtained from Honeywell Inc., Morristown, N.J.;

"Uvitex OB" refers to 2,5-bis(5-tert-butyl-2-benzoxazolyl) thiophene (BBOT), obtained from Ciba Specialty Chemicals (Tarrytown, N.Y.);

"GENIOSIL GF-31" or "GF-31" refers to a 3-methacryloxypropyltrimethoxysilane composition available from Wacker Chemie AG, Munich, Germany;

"Red pigment dispersion" refers to a dispersion containing a red iron III oxide pigment as described in U.S. Provisional Application No. 60/984,785, filed Nov. 2, 2007 (Kalgutkar et al.)

"Yellow pigment dispersion" refers to a dispersion containing a yellow iron III oxide pigment as described in U.S. Provisional Application No. 60/984,785, filed Nov. 2, 2007 (Kalgutkar et al.)

"White pigment dispersion" refers to a dispersion containing a rutile titanium dioxide pigment as described in U.S. Provisional Application No. 60/984,785 filed Nov. 2, 2007 (Kalgutkar et al.).

Sample Preparation

Unless otherwise noted, reagents and solvents were obtained from Sigma-Aldrich Corp., St. Louis, Mo. All mixing of the composites was done by mixing the components in a DAC-150FZ SpeedMixer (Flacktec Corp., Landrum S.C.). Mixing was carried out at progressively higher speeds from 2000 rpm to 2400 rpm for 20 seconds intervals with cooling between mix cycles until no further change in the composite was observed. Camphorquinone, EDMAB and Iodonium hexafluorophosphate were dissolved in the respective resins by rolling the formulation on a roller in a glass bottle until no solids were visible. All composites were filled into syringes and debubbled by applying a load to the plunger for 16 hours at 45° C. The composites were stored and handled under yellow lights.

Disks (3.0 cm×0.11 cm) used for fluorescence testing and measurement of CIELAB parameters and contrast ratios were prepared by pressing composite pastes (prior to photo-curing) in a stainless steel mold at 10,000 psi for 90 seconds. A Carver lab press (Model 3912, Wabash, Ind.) fitted with a quartz-tungsten-halogen curing light was used for this purpose. Photocuring was accomplished either by irradiation in the press under 10,000 psi pressure for 120 seconds (Examples E-5 to E-9) or by removing the sample from the press and photocuring using two dental blue light for 20 seconds repeatedly until the entire area of the disk had been exposed at least once (Examples E-1 to E-4 and Comparative Examples CE-1 to CE-5). In all cases this was followed by irradiation using a high intensity pulsed Xenon light source (Kulzer UniXS, Hanau, Germany) for 90 seconds on each side of the disk.

Measurement of Fluorescence, CIELAB Paraments and Contrast Ratio

Fluorescence stability was tested over a 4 hour period, using equipment and measuring technique for color stability described in ISO 4049:2000. A Hanau sun test apparatus was used with a medium intensity Xe arc lamp. The disks that were exposed to the fluorescence stability test were immersed in water maintained at 37° C. using a circulating bath. Disks were removed from the apparatus and the fluorescence intensity was measured using a Tecan Infinite 200 fluorescence spectrometer (Durham, N.C.). All samples were irradiated at 365 nm and emission data was collected between 390 and 730 nm at 1 nm intervals. The gain was set manually at 70 and each data point was integrated for 20 microseconds with 10 averages. Care was taken to ensure that the same side of the disk that was exposed to the Xe arc lamp was used for the fluorescence measurement. The data was then analyzed as described in Section 3.3.8 in Gunter Wyszecki and W. S. Stiles, "Color Science. Concepts and Methods. Quantitative Data and Formulae.", $2^{nd}$ edition, John Wiley (1982). Data for the 1931 CIE 2° standard observer color matching functions were obtained from the CIE publication CIE 15:2004 (ISBN 3901906339). The results of the analysis are reported in terms of CIE 2° Chromaticity Coordinates and correspond to the perceived color of fluorescence. CIELAB parameters and contrast ratio data was obtained on the same disks using a Hunterlab UltraScan VIS spectrophotometer (Reston, Va.).

Preparation of Silane Treated (S/T) $Y_2SiO_5$:Ce $Y_2SiO_5$:Ce is an inorganic luminescent pigment obtained from Phosphor Technology (Stevenage, Hertfordshire, England) was silane treated with 11.6 wt % of (3-methacryloxy)propyltrimethoxysilane (Genosil GF31) as follow. A slurry of 0.8010 gm of $Y_2SiO_5$:Ce was prepared in 10.0242 gm of 1:1 de-ionized water:1-methoxy-2-propanol solvent with stirring. The pH was adjusted to 2.65 using a few drops of 10% wt trifluoroacetic acid. GF-31 (0.0932 gm) was added all at once and the reaction was run by magnetically stirring the round bottom reaction vessel with a condenser to prevent solvent loss for 5.25 hours at 70° C. The solvent was then stripped off using a rotvap (80° C., vacuum) over 52 minutes to yield S/T $Y_2SiO_5$:Ce as an off-white powder. The powder was ground up using a mortar and pestle and used without further processing.

Preparation of SiO2/ZrO2 Filler 1

Slurry of silica-zirconia nanoclusters (as described in U.S. Pat. No. 6,572,693) was prepared in a 1:1 mixture of de-ionized water and 1-methoxy-2-propanol by magnetic mixing. The pH was adjusted to 3.00 using a few drops of 10% wt trifluoracetic acid. This slurry was silane treated with 17.98 gm of (3-methacryloxy)propyltrimethoxysilane (Genosil GF31) which was added all at once. The reaction was run overnight by rolling the sealed vial at room temperature. The next morning, the slurry was gap dried. The gap drier had a hot plate set point of 290° F., actual entrance of 263° F., exit of 255° F., hot to cold plate gap of approximately 2 inches, coating of 0.015 inches and a line speed of approximately 3 feet per minutes. The powder was passed through a 75 m sieve. No further processing was done prior to use.

Preparation of SiO2/ZrO2 Filler 2

The filler was made by preparing a mixture of 5.47 g of Part A (described below) with 7.93 g of Part B (described below).

Part A was prepared as follows. 31.3590 gm of (3-methacryloxy)propyltrimethoxysilane (Genosil GF31, 11-0021-2849-1) was added to a round bottom flask, next 330.3 gm ethyl acetate and 299.6 gm of silica-zirconia (U.S. Pat. No. 6,572,693) were added to the magnetically mixing flask. Next, 7.21 gm of ammonium hydroxide (28/30%) was added. The reaction was run overnight by magnetically stirring the sealed vial at room temperature. The next day the solvent was stripped off in a rotovap (35° C./vacuum) until most of the solvent was removed, then the bath was turned to 90° C. until the powder was dry by visual inspection. This process took 35 minutes. Next the powder was placed in an 85° C. oven for 2 hours. The powder was passed through a 75 m sieve. No further processing was done prior to use.

Part B was prepared as follows. 38.2841 gm of (3-methacryloxy)propyltrimethoxysilane (Genosil GF31, 11-0021-2849-1) was added to a round bottom flask, next 327.5 gm ethyl acetate and 298 gm of silica-zirconia (U.S. Pat. No. 6,572,693) were added to the magnetically mixing flask. Next, 7.21 gm of ammonium hydroxide (28/30%) was added. The reaction was run overnight by magnetically stirring the sealed vial at room temperature. The next day the solvent was stripped off in a rotovap (35° C./vacuum) until the solvent was removed. This process took 47 minutes. Next the powder was placed in an 85° C. oven for 2 hours. The powder was passed through a 75 m sieve. No further processing was done prior to use.

Examples E1 and E2 and Comparative Examples CE-1 to CE-5

The composites set forth in Table 1 were prepared by the general technique described above (all components listed by weight-percent) in order to compare CIELAB parameters and contrast ratios (measure of opacity) of compositions containing an organic fluorescent pigment, L-88, (examples E-1 and E-2) with those containing an inorganic luminescent pigment, QBK58/UF-A2 (examples CE-1, CE-2, and CE-3) or no fluorescent pigment (examples CE-4 and CE-5). L-88 is an organic fluorescent pigment that is a hydroxyl substituted aryl guanamine. QBK58/UF-A2 is an inorganic luminescent pigment material prepared from $Y_2SiO_5$ with Cerium doping.

TABLE 1

Paste formulations for examples E-1 and E-2 and comparative examples CE-1 to CE-5 (amounts provided in wt-%).

| Component | CE-1 | CE-2 | CE-3 | CE-4 | CE-5 | E-1 | E-2 |
|---|---|---|---|---|---|---|---|
| CAMP | 1.68 | 1.68 | 1.68 | 1.69 | 1.68 | 1.68 | 1.68 |
| BisEDMA 6 | 6.32 | 6.32 | 6.32 | 6.33 | 6.33 | 6.32 | 6.32 |
| UDMA | 1.41 | 1.41 | 1.41 | 1.41 | 1.42 | 1.42 | 1.42 |
| Tris-MAP | 12.40 | 12.40 | 12.39 | 12.42 | 12.41 | 12.40 | 12.39 |
| CPQ | 0.07 | 0.07 | 0.07 | 0.07 | 0.08 | 0.08 | 0.08 |
| IRGACURE 819 | 0.06 | 0.06 | 0.06 | 0.06 | 0.06 | 0.06 | 0.06 |
| ENMAP | 0.38 | 0.38 | 0.38 | 0.38 | 0.38 | 0.38 | 0.38 |
| BHT | 0.03 | 0.03 | 0.03 | 0.03 | 0.03 | 0.03 | 0.03 |
| TINUVIN R-796 | 0.11 | 0.11 | 0.11 | 0.11 | 0.11 | 0.11 | 0.11 |
| $SiO_2$ Filler | 11.61 | 11.60 | 11.60 | 11.62 | 11.62 | 11.61 | 11.61 |
| $ZiO_2$ Filler | 3.87 | 3.87 | 3.87 | 3.87 | 3.88 | 3.87 | 3.87 |
| $SiO_2/ZrO_2$ Filler 1 | 61.91 | 61.88 | 61.85 | 62.00 | 62.00 | 61.94 | 61.90 |
| S/T $Y_2SiO_5$:Ce | 0.15 | 0.20 | 0.25 | 0.00 | 0.00 | 0.00 | 0.00 |
| L-88 | 0.00 | 0.00 | 0.00 | 0.00 | 0.00 | 0.10 | 0.15 |

The CIELAB parameters and contrast ratios for the above formulations were measured using the test protocol set forth above. The results are given in Table 2 (for pastes containing inorganic fluorescent pigment) and Table 3 (for pastes containing organic fluorescent pigment).

TABLE 2

CIELAB parameters and contrast ratio for pastes containing $Y_2SiO_5$:Ce and control without pigment.

| Formulation | % $Y_2SiO_5$:Ce | L* | a* | b* | (Contrast Ratio) |
|---|---|---|---|---|---|
| CE-4 (control) | 0.00 | 86.58 | −2.64 | 12.05 | 33.72 |
| CE-1 | 0.15 | 86.46 | −2.47 | 13.96 | 43.19 |
| CE-2 | 0.20 | 86.96 | −2.42 | 13.56 | 44.29 |
| CE-3 | 0.25 | 86.81 | −2.28 | 14.03 | 46.58 |

TABLE 3

CIELAB parameters and contrast ratio for pastes containing L-88 and control without pigment.

| Formulation | % L-88 | L* | a* | b* | (Contrast Ratio) |
|---|---|---|---|---|---|
| CE-5 (control) | 0.00 | 85.70 | −2.78 | 13.59 | 37.64 |
| E-1 | 0.10 | 86.07 | −3.17 | 12.94 | 36.03 |
| E-2 | 0.15 | 86.36 | −3.46 | 13.14 | 36.73 |

The data in Tables 2 and 3 shows that whereas L-88 has little or no effect on the b* or contrast ratio (opacity), there is a marked effect on both with the addition of $Y_2SiO_5$:Ce. In particular the opacity is at an undesirable level for dental applications and the b* is on the borderline of an undesirable level when at a concentration of 0.25%. The loading level of L-88 required for good fluorescence is much lower than the concentrations used in the experiments. We have surprisingly found that less than 0.05% is needed for good fluorescence. At this desired loading level for L-88, it has little or no effect on the b* and contrast ratio of the composition.

Examples E3 and E4

A timed exposure study for dental composites containing organic dyes and pigments was conducted. Pastes having the formulations set forth in Table 4 were prepared by the general technique described above. These formulations combine L-88, obtained from Beaver Luminescers (Newton, Mass.) with either another fluorescent pigment, A-594-5, obtained from DayGlo Corporation (Cleveland, Ohio), or with an organic fluorescent dye, 2,5-bis(5-tert-butyl-2-benzoxazolyl)thiophene (BBOT), obtained under the trade name Uvitex OB from Ciba Specialty Chemicals (Tarrytown, N.Y.). Samples of each formulation were exposed to UV radiation and the change in fluorescence was measure over time. The Fluorescence decay data was then obtained are shown in Table 5.

TABLE 4

Paste formulations for examples E-3 and E-4 (wt-%).

| Component | E-3 | E-4 |
|---|---|---|
| CAMP | 1.77 | 1.73 |
| BisEMA6 | 6.63 | 6.52 |
| UDMA | 1.49 | 1.55 |
| TrisMAP | 13.05 | 13.54 |
| CPQ | 0.07 | 0.08 |
| IRGACURE 819 | 0.06 | 0.06 |
| ENMAP | 0.40 | 0.39 |
| BHT | 0.04 | 0.03 |
| TINUVIN R-796 | 0.12 | 0.12 |
| $SiO_2$ Filler | 11.37 | 11.13 |
| $ZrO_2$ Filler | 3.79 | 3.71 |
| $SiO_2/ZrO_2$ Filler 2 | 60.63 | 60.79 |
| A-594-5 | 0.360 | 0.000 |
| L-88 | 0.016 | 0.008 |
| Uvitex OB | 0.000 | 0.004 |
| Red Pigment Dispersion | 0.02 | 0.02 |
| Yellow Pigment Dispersion | 0.07 | 0.12 |
| White Pigment Dispersion | 0.13 | 0.21 |

TABLE 5

Fluorescence decay data for dental composites containing organic fluorescent pigments or dyes exposed to UV radiation.

| Time (Minutes) | E-3 cps | E-3 norm | E-4 cps | E-4 norm |
|---|---|---|---|---|
| 0 | 144004 | 1.00 | 266531 | 1.00 |
| 30 | 145495 | 1.01 | 168425 | 0.63 |
| 60 | 134169 | 0.93 | 137441 | 0.52 |
| 120 | 131246 | 0.91 | 90624 | 0.34 |
| 240 | 95651 | 0.66 | 65202 | 0.24 |

Figure 1:
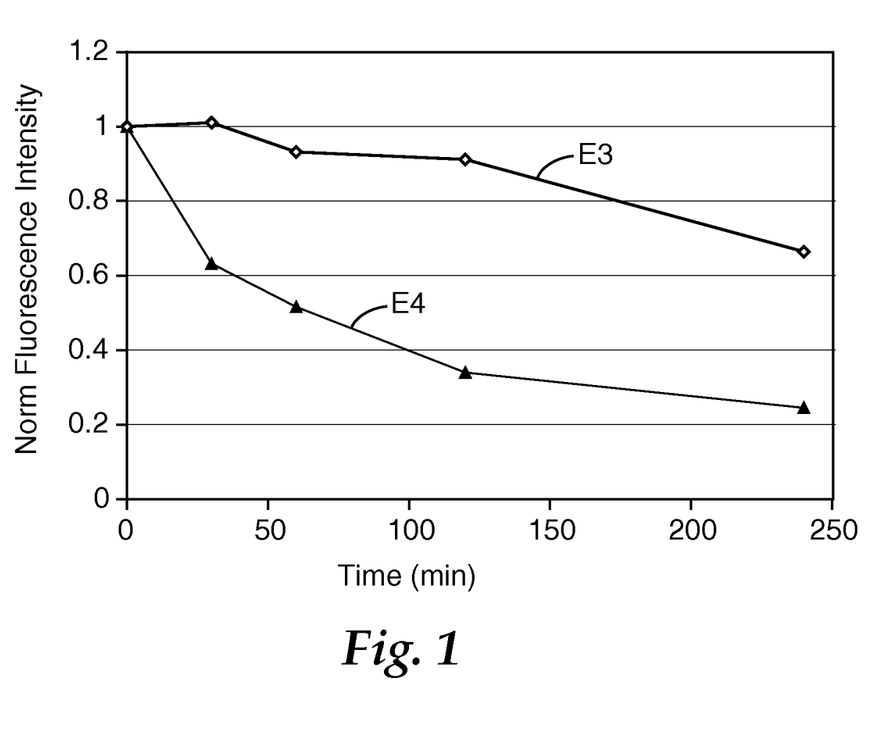
FIG. 1 is a graph showing fluorescence decay data for dental composites subjected to UV exposure.

The data from Table 5, which have been depicted graphically in FIG. 1, show that a formulation containing organic fluorescent pigments, such as A-594-5, resisted fluorescence degradation on UV exposure far better than a formulation containing organic fluorescent dyes. The exact increase in performance depends upon the organic fluorescent pigment used.

Examples E-5 to E-9

Pastes having the formulations set forth in Table 6 were prepared by the general technique described above. These pastes contained combinations of organic fluorescent pigments L-88 and A-594-5 in varying ratios to modulate the perceived color of fluorescence.

TABLE 6

Paste formulations for examples E-5 to E-9

| Component | E-5 | E-6 | E-7 | E-8 | E-9 |
|---|---|---|---|---|---|
| BisGMA | 5.27% | 5.27% | 5.27% | 5.28% | 5.28% |
| TEGDMA | 1.20% | 1.20% | 1.20% | 1.20% | 1.20% |
| UDMA | 7.38% | 7.38% | 7.39% | 7.39% | 7.39% |
| BisEMA6 | 7.38% | 7.38% | 7.39% | 7.39% | 7.39% |
| DPIPF6 | 0.11% | 0.11% | 0.11% | 0.11% | 0.11% |
| CPQ | 0.04% | 0.04% | 0.04% | 0.04% | 0.04% |
| EDMAB | 0.22% | 0.22% | 0.22% | 0.22% | 0.22% |
| BHT | 0.03% | 0.03% | 0.03% | 0.03% | 0.03% |
| TINUVIN R-796 | 0.33% | 0.33% | 0.33% | 0.33% | 0.33% |
| $SiO_2$ FILLER | 7.40% | 7.40% | 7.40% | 7.40% | 7.41% |
| $SiO_2/ZrO_2$ FILLER 3 | 70.45% | 70.48% | 70.51% | 70.53% | 70.55% |
| A-594-5 | 1599 ppm | 1198 ppm | 801 ppm | 398 ppm | 198 ppm |
| L-88 | 403 ppm | 399 ppm | 401 ppm | 400 ppm | 400 ppm |

TABLE 7

Chromaticity Co-ordinates for dental composites containing A-594-5 and L-88.

| Formulation | A-594-5 (ppm) | L-88 (ppm) | x | y | Fluorescence Counts |
|---|---|---|---|---|---|
| E-5 | 1600 | 400 | 0.159 | 0.107 | 525619 |
| E-5 (repeat) | 1600 | 400 | 0.160 | 0.108 | 512282 |
| E-6 | 1200 | 400 | 0.159 | 0.109 | 483245 |
| E-7 | 800 | 400 | 0.160 | 0.111 | 350420 |
| E-8 | 400 | 400 | 0.161 | 0.112 | 350420 |
| E-9 | 200 | 400 | 0.162 | 0.126 | 332637 |

The data in Table 7 show that decreasing the ratio of A-594-5 to L-88 results in an increase in the y Chromaticity Coordinate. This corresponds to more green coloration to the fluorescence. These examples demonstrate that a combination of an organic fluorescent pigment with one or more luminescent agents is useful in tuning the color of fluorescence. Larger changes can be effected by using luminescent agents that have greater differences in their individual fluorescence colors. It should be noted that although the total amount of luminescent agent affects the fluorescence intensity, it does not substantially affect the Chromaticity Coordinates of the fluorescence.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety as if each were individually incorporated.

What is claimed is:

1. A hardenable dental composition comprising a fluorescent benzoxazole organic pigment and a fluorescent hydroxyl substituted aryl guanamine organic pigment.

2. The composition of claim 1, wherein the composition upon hardening has natural tooth fluorescence.

3. The composition of claim 1, wherein at least one of the fluorescent benzoxazole organic pigment and the fluorescent hydroxyl substituted aryl guanamine organic pigment comprises a fluorescent compound encapsulated within or attached to a polymer.

4. The composition of claim 3, wherein at least one of the fluorescent benzoxazole organic pigment and the fluorescent hydroxyl substituted aryl guanamine organic pigment comprises an intrinsically fluorescent organic compound.

5. The composition of claim 1, wherein at least one of the fluorescent benzoxazole organic pigment and the fluorescent hydroxyl substituted aryl guanamine organic pigment is present in an amount less than 1 wt-% of the composition.

6. The composition of claim 1, further comprising a polymerizable component.

7. The composition of claim 6, wherein the polymerizable component comprises an ethylenically unsaturated compound.

8. The composition of claim 7, wherein ethylenically unsaturated compound is a (meth)acrylate.

9. The composition of claim 1, further comprising an initiator system.

10. The composition of claim 9, wherein the composition is photo-curable and the initiator system comprises a photoinitiator.

11. The composition of claim 1, further comprising a filler system.

12. The composition of claim 11, wherein the filler system comprises silica nanoparticles, zirconia nanoparticles, nanoclusters of silica and zirconia nanoparticles, or a combination thereof.

13. The composition of claim 12, wherein the nanoparticles or nanoclusters have been silane treated.

14. A method of making of dental composition having natural tooth fluorescence, the method comprising the steps of:
 (a) providing a dental resin system that, upon curing, provides a material that has a non-natural tooth fluorescence; and
 (b) adding a sufficient amount of a fluorescent benzoxazole organic pigment and a fluorescent hydroxyl substituted aryl guanamine organic pigment to the resin system to provide a composition that, upon curing, has a natural tooth fluorescence.

15. The method of claim 14, further comprising the step of:
 (c) comparing the fluorescence of the composition to the fluorescence of a natural tooth.

16. The method of claim 14, wherein the resin system comprises an ethylenically unsaturated component.

17. The method of claim 16, wherein ethylenically unsaturated component is a (meth)acrylate.

18. The method of claim 14, wherein the composition further comprises an initiator system.

19. The method of claim 18, wherein the composition is photo-curable and the initiator system comprises a photoinitiator.

20. The method of claim 14, wherein the composition further comprises a filler system.

21. The method of claim 20, wherein the filler system comprises silica nanoparticles, zirconia nanoparticles, nanoclusters comprising silica and zirconia nanoparticles, or a combination thereof.

22. The method of claim 21, wherein the nanoparticles have been silane treated.

23. A dental product made by hardening the composition of claim 1.

24. The dental product of claim 23 wherein the dental product is a mill blank.

* * * * *

UNITED STATES PATENT AND TRADEMARK OFFICE
CERTIFICATE OF CORRECTION

| | | |
|---|---|---|
| PATENT NO. | : 9,205,029 B2 | Page 1 of 1 |
| APPLICATION NO. | : 13/123868 | |
| DATED | : December 8, 2015 | |
| INVENTOR(S) | : Rajdeep Kalgutkar | |

It is certified that error appears in the above-identified patent and that said Letters Patent is hereby corrected as shown below:

Title Page, Column 2 (Attorney, Agent or Firm)
Line 1                      Delete "Innovatie" and insert -- Innovative --, therefor.

Title Page, Column 2 (57) ABSTRACT
Line 3                      Delete "an or" and insert -- and/or --, therefor.

Specification

Column 3
Line 67                    After "like" and insert -- . --.

Column 13
Lines 10-11             Delete "unimodial or polymodial" and insert -- unimodal or polymodal --, therefor.
Lines 37-38             Delete "olycarbonates," and insert -- polycarbonates, --, therefor.

Column 17
Line 15                    Delete "phalate," and insert -- phthalate, --, therefor.

Column 18
Line 29                    Delete "(Flacktec" and insert -- (Flacktek --, therefor.

Column 19
Line 19                    Delete "(Genosil" and insert -- (Geniosil --, therefor.
Line 27                    Delete "rotvap" and insert -- rotovap --, therefor.
Line 36                    Delete "trifluoracetic" and insert -- trifluoroacetic --, therefor.
Line 37                    Delete "(Genosil" and insert -- (Geniosil --, therefor.
Line 50                    Delete "(Genosil" and insert -- (Geniosil --, therefor.
Line 64                    Delete "(Genosil" and insert -- (Geniosil --, therefor.

Signed and Sealed this
Fifth Day of July, 2016

Michelle K. Lee
*Director of the United States Patent and Trademark Office*